(12) United States Patent
Delangle et al.

(10) Patent No.: US 8,148,359 B2
(45) Date of Patent: Apr. 3, 2012

(54) CHELATING AGENTS OF METAL IONS, THEIR METHODS OF PREPARATION AND THEIR APPLICATIONS

(75) Inventors: Pascale Delangle, Voiron (FR); Christelle Gateau, Champ sur Drac (FR); Anaïs Pujol, Andernos les Bains (FR)

(73) Assignee: Commissariat a l'Energie Atomique, Paris (FR)

( * ) Notice: Subject to any disclaimer, the term of this patent is extended or adjusted under 35 U.S.C. 154(b) by 427 days.

(21) Appl. No.: 12/403,806

(22) Filed: Mar. 13, 2009

(65) Prior Publication Data

US 2010/0234338 A1  Sep. 16, 2010

(51) Int. Cl.
*A61K 31/33* (2006.01)
*A61K 31/16* (2006.01)
*C07D 255/02* (2006.01)
*C07C 53/00* (2006.01)

(52) U.S. Cl. ......... 514/183; 514/626; 540/474; 562/512
(58) Field of Classification Search ........................ None
See application file for complete search history.

(56) References Cited

OTHER PUBLICATIONS

Tripodal. Chemistry-A European Journal, 1997, 3(8), 1254-68.*

* cited by examiner

*Primary Examiner* — Noble Jarrell
(74) *Attorney, Agent, or Firm* — Alston & Bird LLP

(57) ABSTRACT

The present invention relates to compounds that can be used as metal-ion-chelating agents or as depolluting agents, corresponding to general formula (I) below:

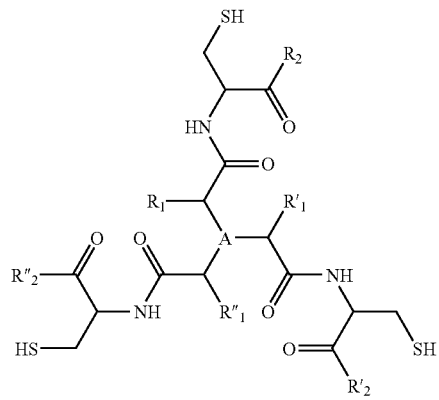

and also to precursor compounds of formula (II) and labelled compounds of formula (III) deriving from the compounds of formula (I). The present invention also relates to the use of the compounds (I), (II) or (III) as a medicament, and also the use thereof for the diagnosis, prevention and treatment of neurodegenerative diseases such as Wilson's disease and Alzheimer's disease.

18 Claims, 1 Drawing Sheet

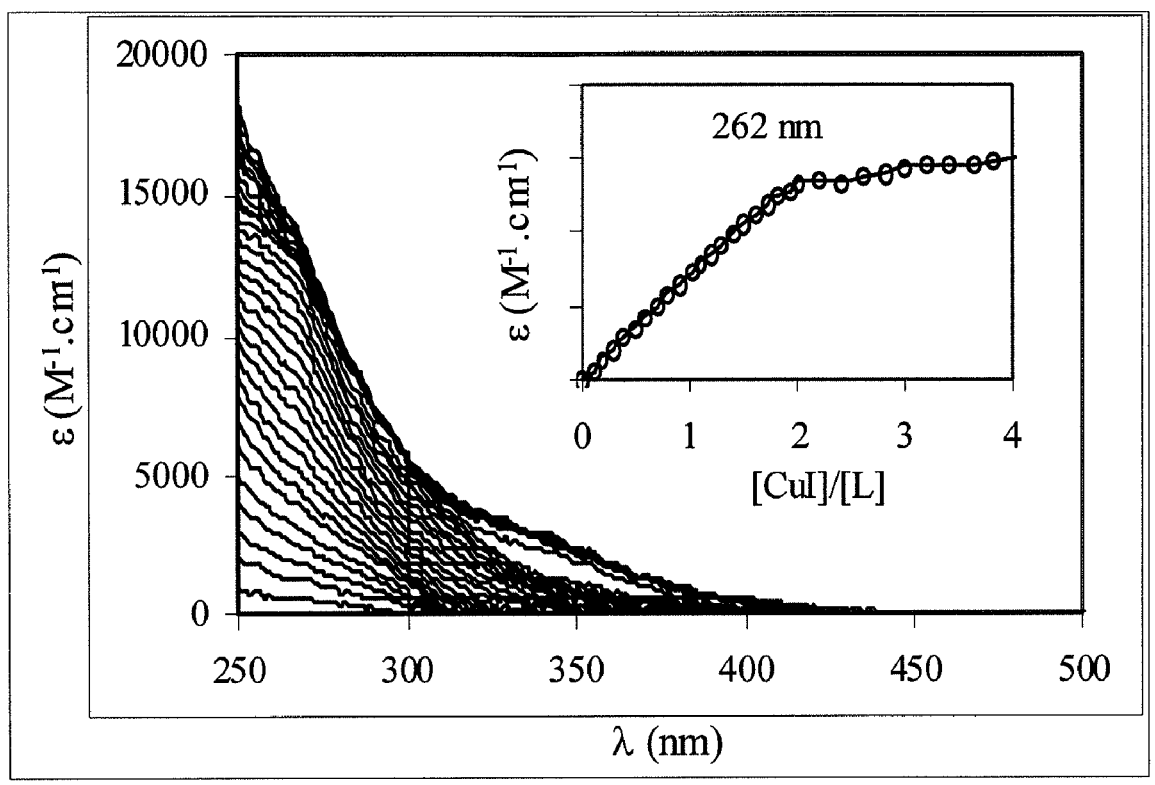

CHELATING AGENTS OF METAL IONS, THEIR METHODS OF PREPARATION AND THEIR APPLICATIONS

The present invention relates to novel compounds of formula (I) that can be used as metal-ion-chelating agents or as depolluting agents, novel compounds of formula (II) that can be used as agents that are precursors of the compounds of formula (I), and also labeled compounds of formula (III), the use of the compounds of formula (I), (II) or (III) as a medicament, and also the use thereof for the diagnosis, prevention and treatment of neurodegenerative diseases, such as Wilson's disease and Alzheimer's disease, and of poisoning with metal ions such as silver, cadmium, cobalt, copper, mercury, nickel, gold, lead and zinc ions.

Diseases related to copper transport dysregulation, such as Wilson's disease, result in an accumulation of copper in the liver, which is the only organ capable of excreting it. Thus, although copper is an element essential to life, it can, in the free state, induce Fenton oxidation reactions and, consequently, prove to be extremely toxic.

More particularly, Wilson's disease is a genetic disease related to a deficiency in a copper transporter, resulting in an accumulation of copper in various regions of the organism (up to 20 times the normal levels), and manifests itself through damage to the liver and to the nervous system. Psychological disorders can also appear with modifications to character, resulting in hyperemotionality with large mood swings, depressive syndromes and psychotic states.

Wilson's disease is induced by mutation of the ATP7B gene, which encodes an ATPase-type transmembrane protein involved in the intracellular and extracellular transport of copper, thus making it possible to regulate the concentration of this metal and the excretion thereof in bile. If the protein is deficient, the metal then accumulates inside the cells. As a general rule, liver damage precedes neurological damage by a few years.

Close to 50% of patients suffering from Wilson's disease are affected by the neurological or psychiatric signs. Magnetic resonance imaging (MRI) shows lesions in several brain structures, even in the absence of any clinical sign, and the size of said lesions appears to correlate with the degree of advancement of the disease.

In extremely serious cases of fulminant hepatitis or in serious damage essentially to the liver, a liver transplant may be envisaged.

At the current time, there are treatments of which the objective comprises eradicating the toxicity of the copper accumulated in the organism.

These treatments must be followed for life, and must never be interrupted. They are based on chelating medicaments which reduce copper absorption in the organism, or which increase the excretion of this metal. The treatments must be subject to periodical monitoring, so as to detect the appearance of adverse side effects.

The existing treatments use various active ingredients, such as:

D-penicillamine (Pen), which increases urinary excretion of copper (G. J. Brewer, DDT, 2005, 10, pp. 1103-1109). D-Penicillamine has a recognized efficacy but its side effects tend to cause it to be replaced with other molecules. In addition, a certain number of recent articles mention a worsening of Wilson's disease with D-penicillamine and suggest restricting the prescription thereof in this indication;

triethylenetetramine (Trien), which is a copper-chelating agent that is often better tolerated than D-penicillamine;

the ammonium tetrathiomolybdate (TTM) anion, absorbed with food, which binds with the copper ions in the digestive tract, preventing the absorption of said ions;

zinc activates the production of proteins, metallothioneins, which will bind the copper in the cells of the intestinal wall (enterocytes), preventing this ion from passing into the bloodstream (B. Sarkar, Chem. Rev., 1999, 99, 2535-2544).

Currently, it is the medicaments based on D-penicillamine, the mechanism of action of which is still poorly understood, which are the most widely used. By virtue of its SH function, D-penicillamine can:

chelate copper and zinc, but also mercury and lead, and increase the urinary excretion thereof, reduce the disulfide bridges of certain molecules: collagen, elastic fibers, immunoglobulins, and thus modify the biological activity thereof, combine with other sulfur-containing molecules, in particular cysteine, thereby forming disulfide bridges.

Other medicaments also exist, the action of which can be likened to D-penicillamine due to the similarity of their pharmacological properties:

pyritinol, which is a symmetrical molecule made up of two parts linked by a disulfide bridge. In the organism, pyritinol is cleaved into two molecules, each comprising an —SH group. However, pyritinol has been used in the treatment of rheumatoid arthritis with indications and adverse effects of the same type as those of D-penicillamine, tiopronin, which is used in the maintenance treatment of rheumatoid arthritis and of cystine stones.

However, there are quite a number of adverse effects of D-penicillamine and of medicaments having a similar mode of action:

early cutaneomucosal adverse effects which are not very serious: erythema, stomatitis, late cutaneomucosal adverse effects which are serious: toxicoderma, pemphigus, dermatomyositis, hematological adverse effects: thrombocytopenia, leukopenia, agranulocytosis, hemolytic anemia, warranting hematological monitoring of the patients treated, digestive adverse effects: ageusia, renal adverse effects: proteinuria.

Metals are also considered to be therapeutic targets of interest for the diagnosis, prevention and treatment of neurodegenerative diseases such as Alzheimer's disease, for which the dysregulation of zinc and copper homeostasis plays an essential role. The copper Cu(II) is complexed and reduced to copper Cu(I) by the APP protein and the Aβ peptide, the copper Cu(I) then accumulating in the amyloid plaques with iron and zinc (E. Gaggelli, H. Kozlowski, D. Valensin, G. Valensin, Chem. Rev., 2006, 106, pp. 1995-2044).

Copper can be in two different oxidation states: copper Cu(I) having an oxidation state +I, which is stable in a reducing medium, and copper Cu(II) having an oxidation state +II, which is stable in an oxidizing medium. The copper present in human cells is mainly copper Cu(I).

Molecules other than D-penicillamine (Pen) can therefore also be used to chelate copper in vivo. They are, for example, 2,3-dimercaptosuccinic acid (DMSA) and 2,3-dimercapto-1-propanesulfonic acid (DMPS) (O. Andersen, Chem. Rev., 1999, 99, pp. 2683-2710), 2,3-dimercaptopropanol (BAL), triethylenetetramine (Trien), the ammonium tetrathiomolybdate (TTM) anion (G. J. Brewer, F. K. Askari, J. Hepatol., 2005, 42, pp. S13-S21) and ethylenediaminetetraacetic acid (EDTA), corresponding to the following semi-developed formulae:

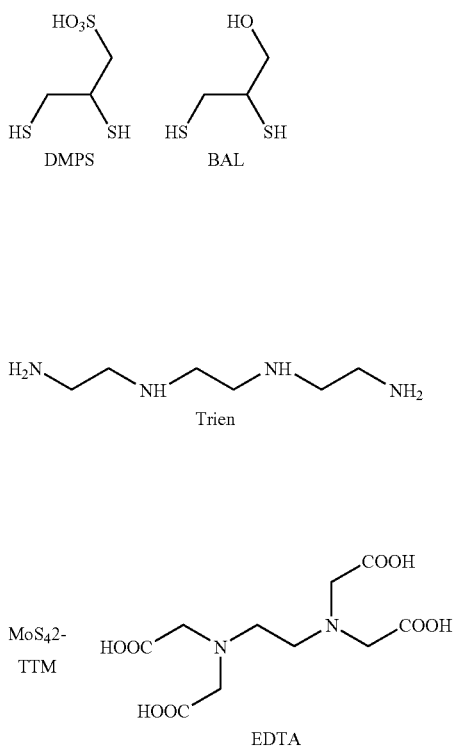

These compounds are known chelating agents for copper Cu(I) and/or for copper Cu(II), blocking the intestinal absorption of copper.

However, these compounds result in adverse side effects, and do not enable the treatment of patients for whom the diseases have been detected at an already advanced stage (non-early detection), and for whom there is a considerable intracellular accumulation of copper.

Furthermore, some chelating agents, such as Trien and EDTA, are very strong chelating agents, which chelate many metal ions, and one of the main drawbacks of which is their lack of selectivity.

Thus, there exists today a need for chelating agents which are more selective, in particular with regard to intracellular copper Cu(I), and especially less toxic, the side effects of which will be less violent than those of the molecules currently used.

The inventors have found, surprisingly, that the novel compounds of the invention described hereinafter appear to be a better alternative, in particular in terms of selectivity, compared with the molecules previously developed, for the diagnosis, prevention and treatment of neurodegenerative diseases and of poisoning with metal ions such as silver, cadmium, cobalt, copper, mercury, nickel, gold, lead and zinc ions.

Thus, the present invention relates to novel compounds of formula (I) that can be used as metal-ion-chelating agents or as depolluting agents, to novel compounds of formula (II) that can be used as agents that are precursors of the compounds of formula (I) of the invention, and to labelled compounds of formula (III). A subject of the present invention is also the use of the compounds of formula (I), (II) or (III) as a medicament, and also the use thereof for the diagnosis, prevention and treatment of neurodegenerative diseases, such as Wilson's disease and Alzheimer's disease.

The compounds of the invention can thus be used for the diagnosis and prevention of neurodegenerative diseases in individuals exhibiting a higher risk due to genetic or environmental factors.

A subject of the present invention is therefore novel compounds of formula (I) that can be used as metal-ion-chelating agents, said compounds of formula (I) being derivatives of nitrilotriacetic acid (NTA) or of 1,4,7-triazacyclononane-1,4,7-triacetic acid (NOTA), NTA and NOTA being already known for complexing metal ions in many industrial or medical applications.

NTA is an aminotricarboxylic acid, the empirical formula of which is $C_6H_9NO_6$, and which can bind to metal ions, such as the ions of alkali metals or alkaline-earth metals, the metal ions of blocks d, f and p of Mendeleev's periodic table, and more particularly $Ca^{2+}$, $Cu^{2+}$, $Mg^{2+}$, or $Fe^{3+}$ ions, so as to form water-soluble complexes. This chelating agent is normally used to sequester calcium and magnesium ions in detergents (as a replacement for phosphates), in the treatment of water so as to prevent scaling, but also for the manufacture of textiles or the production of paper, this compound being readily biodegradable and readily degradable by chemical or photochemical reaction. NTA is also known as a therapeutic chelating agent for the treatment of manganese poisoning or for the treatment of iron overload (Kaur G., Hasan S. K. and Srivastava R. C., Arch. Toxicol., 45: 203 (1980); Pollack S. and Ruocco S., Blood, 57(6): 1117 (1981)).

NOTA is a cyclic organic compound of formula $C_{12}H_{21}N_3O_6$, which derives from cyclononane in which three equidistant $CH_2$ groups have been replaced with $N-CH_2-COOH$ groups. NOTA is a hexadentate ligand, which means that it has six atoms capable of binding to metal ions. This chelating agent is also very widely used in detergent compositions and for water treatment.

Thus, the first subject of the present invention concerns the compounds of formula (I) below:

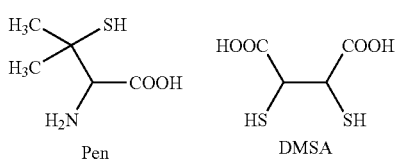

(I)

in which the group A represents:
either a nitrogen atom,
or a ring corresponding to the formula below, and in which the substitution takes place on the nitrogen atoms:

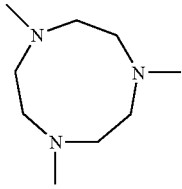

and in which:
the $R_1$, $R'_1$ and $R''_1$ radicals, which may be identical or different, represent a hydrogen atom or an optionally substituted alkyl radical containing 1 to 12 carbon atoms, the $R_1$, $R'_1$ and $R''_1$ radicals preferably being hydrogen atoms,
the $R_2$, $R'_2$ and $R''_2$ radicals, which may be identical or different, are chosen from —OH, —OR, —NHR and —NRR' groups in which R and R', which may be identical or different, represent a hydrogen atom or an optionally substituted alkyl radical containing 1 to 12 carbon atoms, the $R_2$, $R'_2$ and $R''_2$ radicals preferably being —$NH_2$, —OH or —OR groups in which R represents a hydrogen atom or an optionally substituted alkyl radical containing 1 to 12 carbon atoms, and even more preferably an ethyl radical.

When the group A of the compounds of formula (I) represents a nitrogen atom, i.e. when the compounds of formula (I) of the invention are derived from NTA, said compounds can be represented by a structure of specific formula ($I_a$):

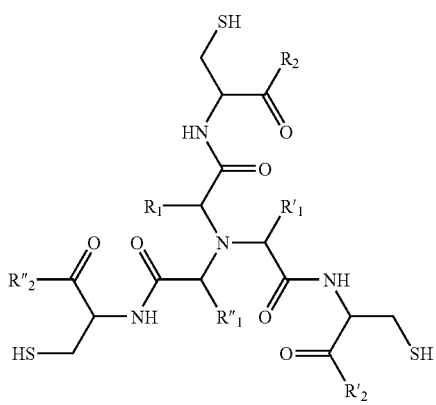

When the compounds of the invention correspond to the structure ($I_a$), the $R_2$, $R'_2$ and $R''_2$ radicals can advantageously be —$NH_2$ or —OH groups or —OR groups in which R represents a hydrogen atom or an optionally substituted alkyl radical containing 1 to 12 carbon atoms. Even more preferably, R is an ethyl group.

The method for preparing the compounds of formula ($I_a$) of the invention can then be generalized according to the following reaction scheme:

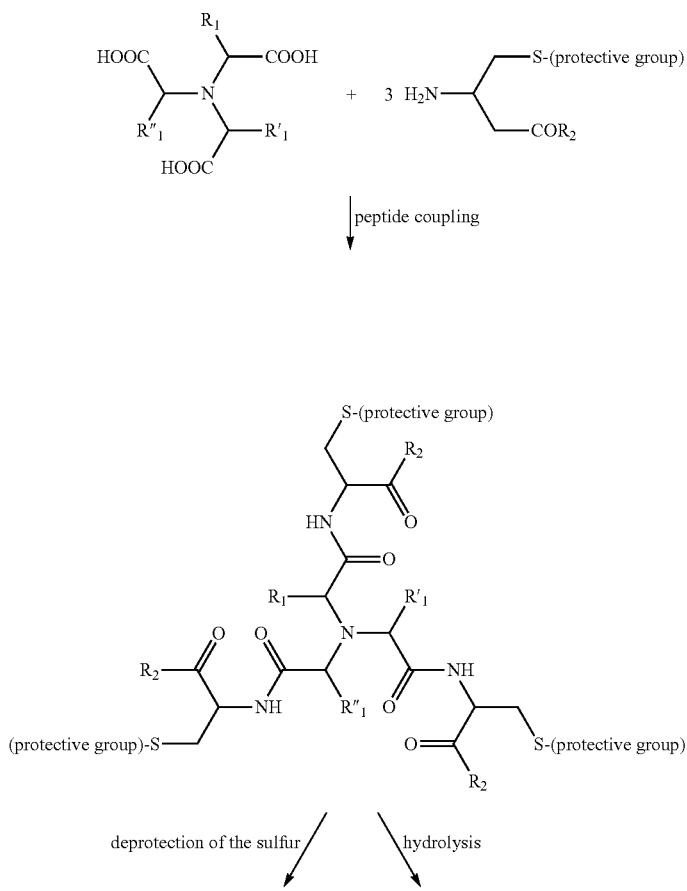

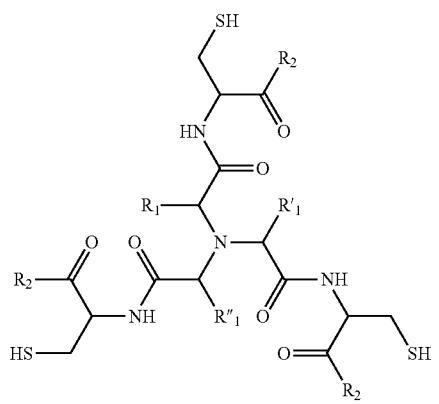

(Ia)

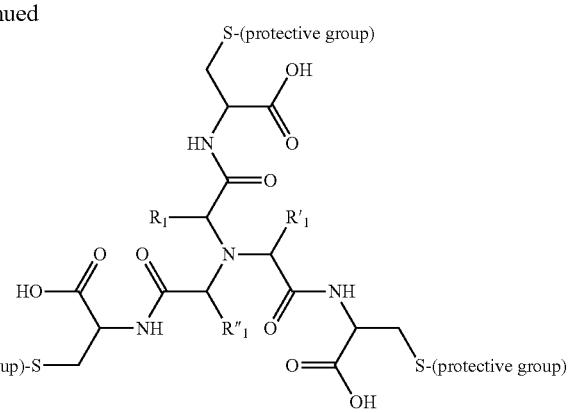

↓ deprotection of the sulfur

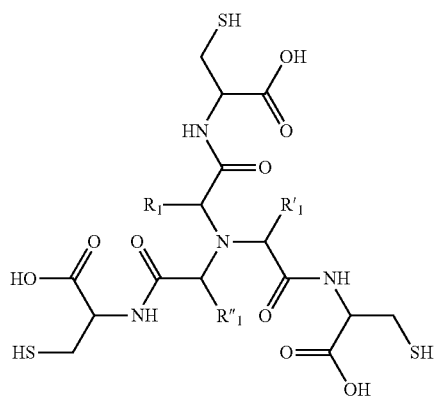

(Ia) in which $R_2$, $R'_2$ and $R''_2$ represent an —OH group

The thiol-function-protecting groups are well known to those skilled in the art, and can be chosen from those mentioned in the reference manual *Protective groups in Organic Synthesis* by T. W. Greene and P. G. M. Wuts, 3rd edition, Wiley, 1999. The protective groups that are the most preferred are chosen from triphenylmethane —$C(C_6H_5)_3$, tert-butyl —$C(CH_3)_3$, thio-tert-butyl —S—$C(CH_3)_3$, 3-nitro-2-pyridinesulfonyl (Npys) and acetamidomethyl —$CH_2NHCOCH_3$ groups, each of these groups having its own method of deprotection as described in the reference mentioned above.

The present invention also concerns a method for preparing the compounds of formula ($I_a$), comprising the following stages:

(i) reacting one equivalent of nitrilotriacetic acid (NTA) with three equivalents of a cysteine derivative of formula:

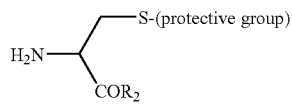

in the presence of a polar solvent, such as dimethylformamide, dichloromethane, chloroform, methanol or ethanol, preferably at a temperature of between −10° C. and 30° C., for a period of typically between 12 and 48 hours, (ii) optionally, hydrolyzing the —$COR_2$ function of the product obtained during stage (i) to give an acid function by addition of a strong base, such as lithium hydroxide (LiOH), sodium hydroxide (NaOH) or potassium hydroxide (KOH), the amount of strong base added preferably being equal to four equivalents, (iii) deprotecting the —S-(protective group) function to give a thiol —SH function, it being possible for said deprotection to be carried out by addition of a large excess of a strong acid, such as trifluoroacetic acid when the protective group is triphenylmethane $C(C_6H_5)_3$, preferably at a temperature of between 20° C. and 40° C. for a period of typically between 15 minutes and 1 hour.

When the group A of the compounds of formula (I) represents a ring derived from triazacyclononane, i.e. when the compounds of formula (I) of the invention are derived from NOTA, they can be represented by a structure of specific formula ($I_b$):

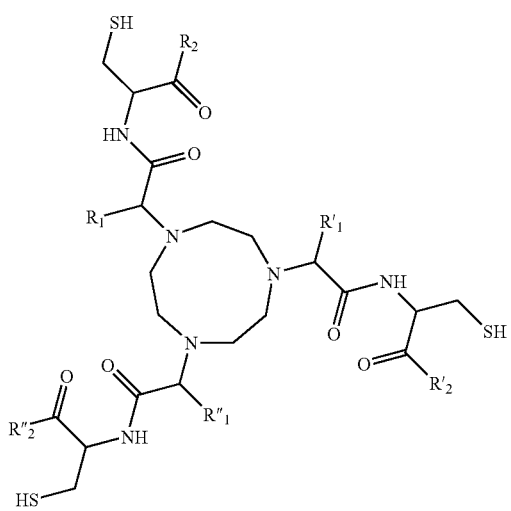

(1$_b$)

When the compounds of the invention correspond to the structure ($I_b$), the $R_2$, $R'_2$ and $R''_2$ radicals can advantageously be —$NH_2$ or —OH groups or —OR groups in which R represents a hydrogen atom or an optionally substituted alkyl radical containing 1 to 12 carbon atoms. Even more preferably, R is an ethyl group.

The method for preparing the compounds of formula ($I_b$) of the invention can then be generalized according to the following reaction scheme ($R_1$=$R'_1$=$R''_1$):

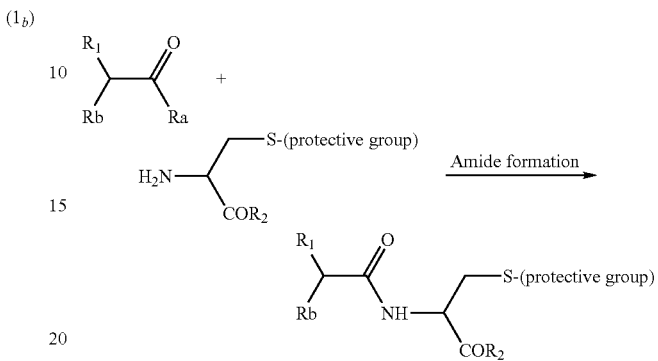

wherein:
- $R_a$ is selected from halogen atoms, preferably chlorine or bromine atoms, hydroxyl —OH groups and —$OCOR_{a'}$ groups in which $R_{a'}$ represents an alkyl group containing 1 to 12 carbon atoms, $R_{a'}$ preferably being a methyl or ethyl group,
- $R_b$ is a leaving group selected from halogen atoms, preferably chlorine or bromine atoms, tosylate groups such as para-toluenesulfonate, and mesylate groups such as methanesulfonate or trifluoromethanesulfonate.

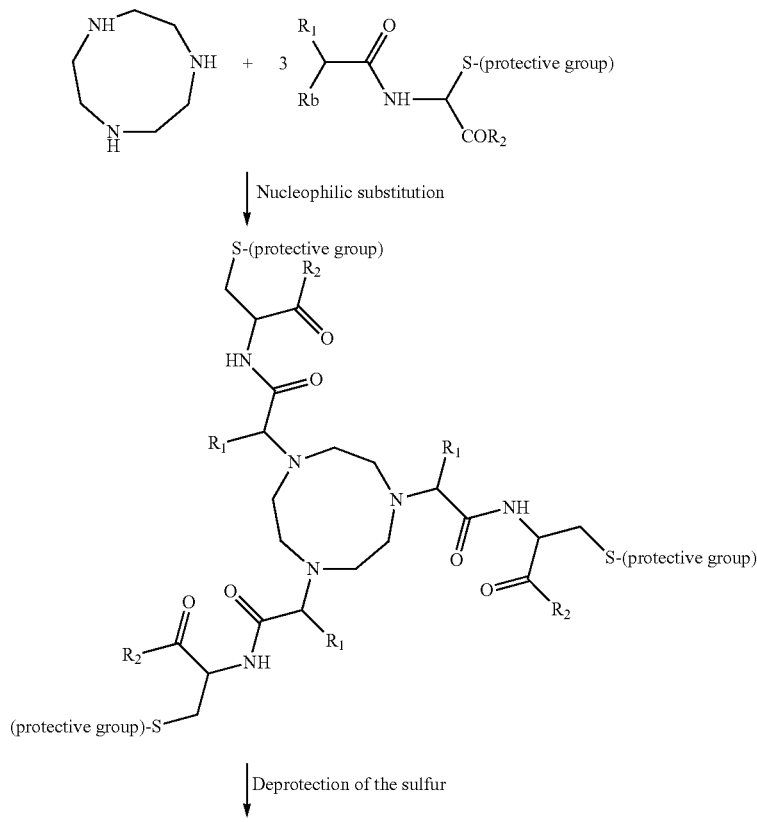

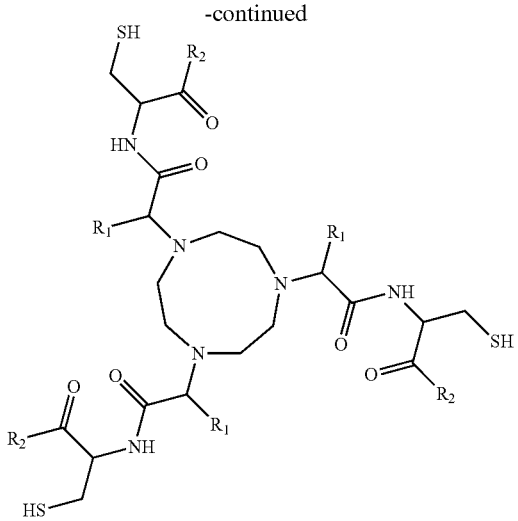

The present invention also concerns a method for preparing the compounds of formula ($I_b$), comprising the following stages:
(i) reacting one equivalent of a molecule $R_bCHR_1C(O)R_a$ ($R_a$ and $R_b$ being as defined above) with one equivalent of a cysteine derivative of formula:

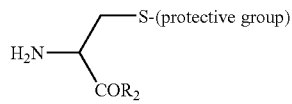

in the presence of a weak base, such as potassium hydrogen carbonate ($KHCO_3$), sodium hydrogen carbonate ($Na_2CO_3$), potassium carbonate ($K_2CO_3$), sodium carbonate ($Na_2CO_3$) and tertiary amines, such as diisopropylethylamine ((($CH_3)_2HC)_2$—N—$CH_2CH_3$) or triethylamine ($N(CH_2CH_3)_3$), and in a solvent medium, it being possible for said solvent to be chosen from polar solvents such as dichloromethane, chloroform, ethyl acetate, acetonitrile, dimethylformamide and water, preferably at a temperature of between −10° C. and 10° C. for a period of typically between 30 minutes and 2 hours,
(ii) reacting one equivalent of 1,4,7-triazacyclononane (TCN) with three equivalents of a bromoacetamide derivative, obtained during stage (i), of formula:

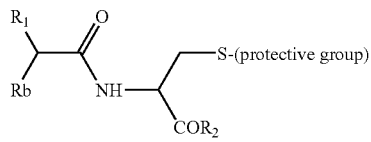

in the presence of a weak base, such as potassium hydrogen carbonate ($KHCO_3$), sodium hydrogen carbonate ($Na_2CO_3$), potassium carbonate ($K_2CO_3$), sodium carbonate ($Na_2CO_3$) and tertiary amines such as diisopropylethylamine ((($CH_3)_2HC)_2$—N—$CH_2CH_3$) or triethylamine ($N(CH_2CH_3)_3$), and in a solvent medium, it being possible for said solvent to be chosen from dichloromethane, chloroform, ethyl acetate, acetonitrile and dimethylformamide, (iii) deprotecting the —S-(protective group) function to give a thiol —SH function, it being possible for said deprotection to be carried out by the addition of a large excess of a strong acid, such as trifluoroacetic acid when the protective group is triphenylmethane $C(C_6H_5)_3$, preferably at a temperature of between 20° C. and 40° C. for a period of typically between 15 minutes and 1 hour.

Another subject of the invention concerns the use of the compounds of formula (I) of the invention, as chelating agents for metal ions of Mendeleev's periodic table, more preferably as chelating agents for soft and intermediate ions as defined in R. G. Pearson, J. Am. Chem. Soc., 1963, vol. 85, pp. 3533-3539, and even more preferably as chelating agents for Ag(I), Cd(II), Co(II), Cu(I), Hg(II), Ni(II), Au(I), Pb(II) and Zn(II) ions, and more particularly for intracellular copper Cu(I) ions.

Another possible use of the compounds of formula (I) of the invention is the use thereof as depolluting agents for depolluting water contaminated with metals. When the compounds of formula (I) of the invention are used as depolluting agents, the depolluting is then preferably carried out in a reducing medium. The limiting pH value of the medium depends on the metal ion to be complexed. Thus, for Hg(II) and Cu(I) ions, the pH of the reducing medium is preferably greater than or equal to 1, and for Zn(II), Pb(II) and Cd(II) ions, the pH of the reducing medium is preferably greater than or equal to 4 or 6.

The present invention also concerns compounds that can be used as agents that are precursors of the compounds of formula (I), corresponding to formula (II) below:

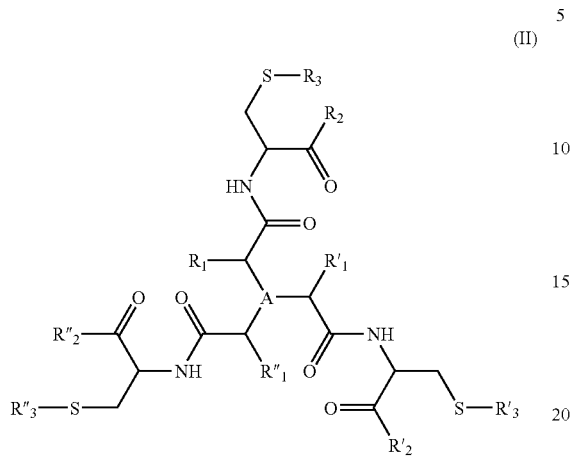
(II)

in which the group A and the $R_1$, $R'_1$, $R''_1$, $R_2$, $R'_2$ and $R''_2$ radicals have the same meaning as above, and in which:

the $R_3$, $R'_3$ and $R''_3$ radicals, which may be identical or different, make it possible to protect the precursor agents while at the same time having masked complexation properties, and represent a group —S—W or —S-E-L, wherein:

S is a sulfur atom,

W is an optionally substituted alkyl radical containing 1 to 12 carbon atoms,

E is a spacer arm that can be selected from optionally substituted alkyl groups containing 1 to 12 carbon atoms, and polyols such as polyethylene glycol preferably having 1 to 8 oxyethylene OE units, L is a biological ligand, and preferably a hepatic or neuronal cell ligand, selected from sugars such as glucose, galactose and N-acetylgalactose.

Thus, the compounds of formula (II) of the invention that are used as precursor agents can also be likened to prodrugs having masked complexation properties via their masked thiol functions.

The method for preparing the compounds of formula (II) of the invention can be generalized according to the following reaction scheme:

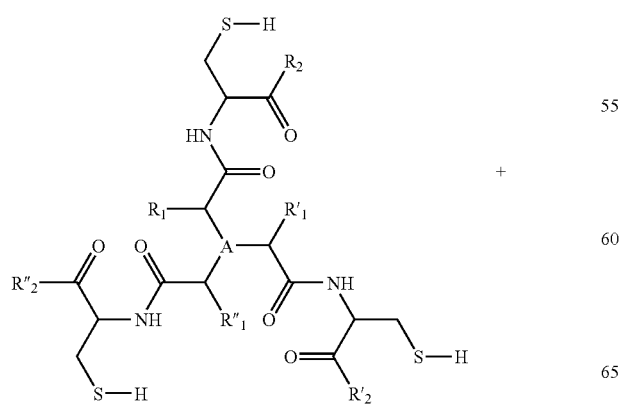

+

V—S-E-L ⟶

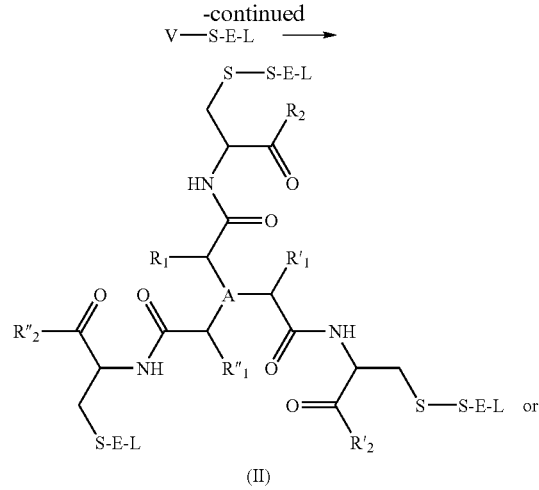
(II)

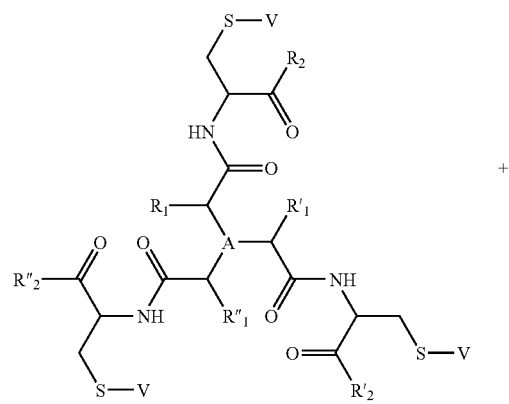

+

H—S-E-L ⟶

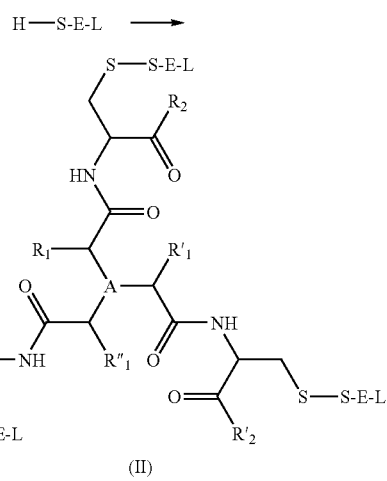
(II)

wherein V is a group for activating the formation of S—S disulfide bridges, chosen from tosyl groups, phenyl, and in particular ortho-nitrophenyl, groups, tolyl, and in particular para-tolyl, groups, 2-pyridinesulfonyl groups, and in particular the 3-nitro-2-pyridinesulfonyl group (Npys), and any other similar, optionally substituted aromatic group.

The compounds of formula (II) of the invention are converted, in a reducing medium, to compounds of formula (I), according to the following reaction:

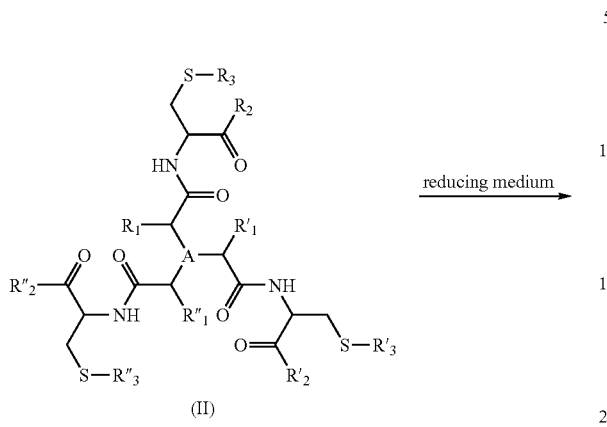

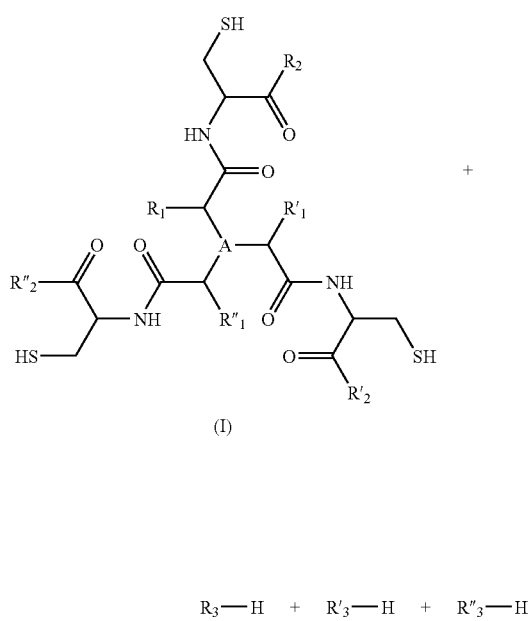

said reaction allowing the release of the thiol functions and, consequently, the release of the chelating agents in the organism, and more particularly in the targeted cells.

The reducing agent for obtaining the compounds of formula (I) may be a molecule carrying a thiol function, such as ethanedithiol (EDT), glutathione (GSH) or dithiotreitol (DTT), ascorbic acid or a salt thereof, or a molecule carrying a phosphine function, such as tri(2-carboxyethyl)phosphine (TCEP).

Thus, the release of the chelating agents is carried out by reduction in vivo in the organism, for example in the hepatic cells where glutathione, which is present at approximately 1 mM, can play the role of reducing agent, or for example in the brain where ascorbate, which is present at approximately 200-400 μM, can also play the role of reducing agent.

A subject of the present invention is also labelled compounds corresponding to formula (III) below:

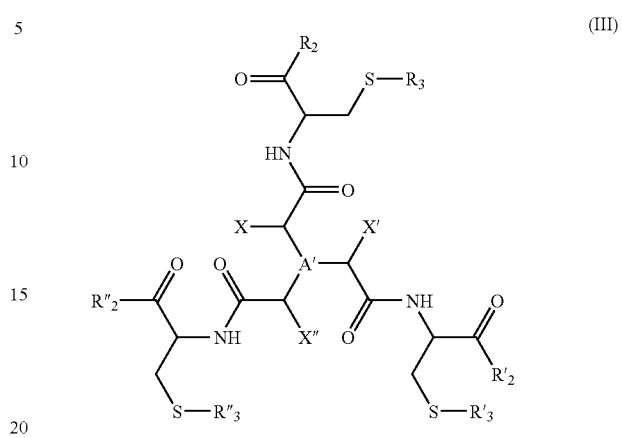

in which the group A' represents:
either a nitrogen atom,
or a ring corresponding to the formula below, and in which the substitution takes place on the nitrogen atoms:

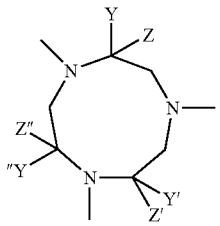

in which the $R_2$, $R'_2$ and $R''_2$ radicals have the same meaning as above, and in which:
the $R_3$, $R'_3$ and $R''_3$ radicals, which may be identical or different, represent a group —S—W or —S-E-L, wherein:
S is a sulfur atom,
W is an optionally substituted alkyl radical containing 1 to 12 carbon atoms,
E is a spacer arm that can be selected from optionally substituted alkyl groups containing 1 to 12 carbon atoms, and polyols such as polyethylene glycol preferably having 1 to 8 oxyethylene OE units,
L is a biological ligand, and preferably a hepatic or neuronal cell ligand, selected from sugars such as glucose, galactose and N-acetylgalactose,
the groups X, X', X", Y, Y', Y", Z, Z' and Z", which may be identical or different, represent a hydrogen atom or a label, provided that at least one of said groups X, X', X", Y, Y', Y", Z, Z' or Z" is a label.

The term "label" is intended to mean any entity capable of being detected by suitable means, the labels used in the context of the invention typically corresponding to the labels used by those skilled in the art in the biology field for labeling biological molecules of interest, in particular in the context of carrying out a diagnosis, of carrying out galenical studies, or alternatively of monitoring the metabolization of active compounds. The labeling may be direct in nature, and in this case the label is termed a "direct label" and has at least one detectable physical property, or the labeling may be indirect in nature, and in this case the label is termed an "indirect label"

and is capable of reacting selectively with a third entity, it being possible for the latter either to have at least one detectable physical property, for instance an antibody having a fluorescent activity, or to be involved in a reaction process at the end of which a physical property may be detected, for instance when the product of degradation of the entity can have at least one detectable physical property such as fluorescence. The indirect labeling is often carried out using antibodies or nanoparticles having a fluorescent activity. In this case, the indirect label of the compounds of formula (III) has an affinity for the third entity.

Thus, the label of the invention may be either a chemical entity which is organic in nature, or a chemical entity which is inorganic in nature, such as a complex or a crystal, it being possible for the latter to be optionally coated with an organic layer, this chemical entity that is inorganic in nature being generally of sufficiently small size, typically on the nanometric scale, so as not to disturb the biological system into which it is introduced.

The directly or indirectly detectable physical property may be a reactivity that is specific with respect to an electromagnetic source such as a magnetic field, for example through magnetic resonance imaging, or with respect to light radiation that can be focused, for example through fluorescence imaging with fluorophores, or else with respect to nuclear radiation, for instance using isotopes.

The labels that are the most preferred are the direct labels, and more particularly fluorophores. Typically, they are organic fluorophores or nanoparticles.

The fluorophores used in the context of the invention may be aromatic fluorescent compounds of which the π-π transitions are characterized by high fluorescence quantum yields and molar absorption coefficients, it being possible for said fluorophores to be chosen from rhodamine, fluorescein, pyronin, coumarin, benzophenone, anthrone, fluorenone, pyridine, quinoline, acridine, naphthalene, anthracene, naphthacene, pentacene, xanthene and derivatives thereof.

The various groups of labels and the various associated detection techniques are known to those skilled in the art and described in the textbook *Anti-Cancer Agents in Medicinal Chemistry*, 2008, 8, 497-522. More specifically, it is possible to refer to the fluorophores mentioned in *Cytometry Part A* 69A: 863-871 (2006) and to the nanoparticles mentioned in the documents *Anal. Bioanal. Chem.*, 384: 620-630 (2006).

Thus, the labelled compounds of formula (III) of the invention can be used for visualizing the course taken by said compounds in the organism, by luminescence.

Another subject of the invention concerns the use of the compounds of formula (I), (II) or (III) of the invention for the application thereof as a medicament, and in particular for the application thereof as a medicament for the diagnosis, prevention and treatment of neurodegenerative diseases, such as Wilson's disease and Alzheimer's disease.

A further subject of the present invention concerns the use of the compounds of formula (I), (II) or (III) of the invention for the application thereof as a medicament for the diagnosis, prevention and treatment of poisoning with metal ions such as silver, cadmium, cobalt, copper, mercury, nickel, gold, lead or zinc ions, and even more preferably with intracellular copper Cu(I) ions, poisoning with such ions generally resulting in severe inflammations, renal deficiencies, hemorrhages, severe neurological disorders of the central nervous system; the term saturnism is then used in the case of lead poisoning and the term hydrargyria (or hydrargyrism) is then used in the case of mercury poisoning.

Finally, a subject of the present invention is also a pharmaceutical composition comprising, as active ingredient, at least one compound (I), (II) or (III) as defined above and at least one pharmaceutically acceptable carrier.

Said pharmaceutical compositions include both compositions in solid form (tablets, gel capsules, capsules, etc.) and compositions in liquid form (solutions, suspensions or emulsions) and include the excipients suitable for oral, topical or parenteral administration.

The administration of the compounds or the compositions according to the invention is preferably carried out orally or parenterally (intravenously by drip or injection, in particular).

The doses of compounds are preferably less than 2 g of product per day, and vary according to the formulation selected, the method of administration and the poisoning or the disease to be treated. Other factors, such as age, weight, height, gender and also certain biological parameters (excretion rate, combination with other medicaments, allergies, etc.) are also to be taken into account.

In addition to the above arrangements, the invention also comprises other arrangements which will emerge from the further description which follows, which relates to examples demonstrating the complexing properties of the compounds of the invention, and also to the attached drawing in which:

FIG. 1 represents the UV quantitative determination of NTA(CysOC$_2$H$_5$)$_3$ (compound 4) with Cu(CH$_3$CN)PF$_6$ in a 20 mM phosphate buffer solution, of pH=7.4, at a temperature of 298 K.

STARTING MATERIALS

TABLE I

| Compound | Supplier |
| --- | --- |
| Nitriloacetic acid (NTA) | Sigma-Aldrich |
| N-Ethyl-N'-(3-dimethylaminopropyl)-carbodiimide | Sigma-Aldrich |
| 1-Hydroxybenzotriazole hydrate | Sigma-Aldrich |
| Bromoacetyl bromide | Sigma-Aldrich |
| 1,4,7-Triazacyclononane-trihydrochloride | CheMatech |
| Bathocuproine disulfonate (BCS) | Sigma-Aldrich |
| 5,5'-Dithiobis-2-nitrobenzoic acid (DNTB) | Acros |
| Dimethylformamide (DMF) | Sigma-Aldrich |
| Ethyl acetate (CH$_3$COOC$_2$H$_5$) | Riedel de Haën |
| Sodium hydrogen carbonate (NaHCO$_3$) | Prolabo |
| Sodium sulfate (Na$_2$SO$_4$) | Carlo Erba |
| Ethanol | Carlo Erba |
| Lithium hydroxide (LiOH) | Sigma-Aldrich |
| Hydrochloric acid (HCl) | Sigma-Aldrich |
| Trifluoroacetic acid (TFA) | Riedel de Haën |
| Triethylsilane (HSiC$_2$H$_5$)$_3$ | Sigma-Aldrich |
| Dichloromethane (CH$_2$Cl$_2$) | Sigma-Aldrich |
| Potassium bicarbonate (KHCO$_3$) | Sigma-Aldrich |
| Potassium carbonate (K$_2$CO$_3$) | Sigma-Aldrich |
| Anhydrous acetonitrile (CH$_3$CN) | Sigma-Aldrich |
| Ethylenediaminetetraacetic acid (EDTA) | Fischer Chemicals |

The starting materials were used without further purification.

The aqueous solutions were prepared using an ultrapure water, obtained by filtration and purification by reverse osmosis using a Millipore Milli-Q® cartridge (resistivity 18 MΩ.cm).

Characterization Methods:

1/ Thin Layer Chromatography (TLC)

The TLC is carried out on a silica 60 F254 gel (supplier: Merck).

2/ Flash Chromatography

The flash chromatography is carried out on a silica 60 gel of thickness 40-63 µm (supplier: Merck).

3/ High Performance Liquid Chromatography (HPLC)

The HPLC chromatography is carried out on a VWR system equipped with RP18 columns (L=250 mm, Ø=4.6 mm and p=5 µm for the analytical column; L=250 mm, Ø=50 mm and p=10 µm for the preparative column).

The flow rates used are 1 ml/min for the analytical column and 75 ml/min for the preparative column, with UV detection at 214 nm.

The elution conditions are the following:
  solvent A: mixture of water/trifluoroacetic acid (TFA) (99.925/0.075),
  solvent B=$CH_3CN$/water/trifluoroacetic acid (TFA) (90/10/0.1).

4/ NMR Analyses

The $^1H$ and $^{13}C$ NMR spectra were recorded on a Mercury Varian 400 spectrometer and on a Bruker Avance 500 spectrometer.

The chemical shifts are indicated in ppm with the solvent as internal reference.

5/ Mass Spectra

The mass spectra were recorded on a Finigan LCQ-ion trap apparatus equipped with an electron source.

The elemental analyses were carried out by the Service Central d'Analyse [Central Analysis Service] (Solaize, France).

6/ UV-Visible Spectroscopy

The UV-visible spectra were recorded on a Varian Cary 50 spectrophotometer.

7/ Circular Dichroism

The circular dichroism spectra were recorded with a Chirascan spectrophotometer (Applied Photophysics®).

1/ Syntheses

Synthesis of the Molecule $HCysC(C_6H_5)_3OC_2H_5$:

The $HCysC(C_6H_5)_3OC_2H_5$ molecule was synthesized using L-cysteine according to the procedure described in the publication Bolzati et al., Bioconjugate chem., 2003, 14, 1231.

EXAMPLE 1

Synthesis of Compound 1: $NTA(CysC(C_6H_5)_3OC_2H_5)_3$

Nitriloacetic acid (0.196 g, 1.03 mmol) is added to a solution of $HCysC(C_6H_5)_3OC_2H_5$ (1.200 g, 3.06 mmol) in 20 ml of dimethylformamide (DMF). The mixture is then cooled to a temperature of 0° C., and N-ethyl-N'-(3-dimethylaminopropyl)carbodiimide (0.587 g, 3.06 mmol) and 1-hydroxybenzotriazole hydrate (0.414 g, 3.06 mmol) are successively added. The reaction mixture is then mixed at ambient temperature for 24 h under argon.

After evaporation of the solvent, the residue is then dissolved in 100 ml of ethyl acetate. The organic phase is then washed with 2×50 ml of water, then 50 ml of a saturated solution of sodium hydrogen carbonate ($NaHCO_3$) and 2×50 ml of a saturated solution of sodium chloride (NaCl).

The organic phase is then dried with sodium sulfate ($Na_2SO_4$), and then concentrated under reduced pressure (20 mbar).

The resulting product (1.391 g) is purified by silica gel chromatography (100 ml, eluent: 80/20 $CH_2Cl_2$/ethyl acetate), so as to give compound 1 (1.103 g, yield=82%) in the form of a white powder.

$^1H$ NMR ($CD_3CN$, 400 MHz, 298 K): δ=1.05 (t, J=7.0 Hz, 9H, $CH_3$); 2.39 and 2.68 (ABX, $J_{BX}$=4.1 Hz, $J_{AX}$=8.0 Hz, $J_{AB}$=12.7 Hz, 6H, $CH_2S$); 3.17 and 3.29 (AB, $J_{AB}$=15.0 Hz, 6H, $CH_2CO$); 3.84 and 3.96 (ABX$_3$, $J_{AX}$=7.0 Hz, $J_{BX}$=7.0 Hz, $J_{AB}$=10.9 Hz, 6H, $CH_2CH_3$); 4.34 (td, J=4.0 and 8.2 Hz, 3H, CH); 7.13-7.17 (m, 30H, $SC(C_6H_5)_3$); 7.22 (d, J=7.4 Hz, 15H, $SC(C_6H_5)_3$); 7.56 (d, J=8.6 Hz, 3H, NH).

$^{13}C$ NMR ($CD_3CN$, 100 MHz, 298 K): δ=14.39 ($CH_3$); 33.69 ($CH_2S$); 52.11 (CH); 57.97 ($CH_2CO$); 62.21 ($CH_2CH_3$); 129.90-127.16 (($C_6H_5)_3$); 144.70 ($C(C_6H_5)_3$); 171.66 and 170.70 (2*CO).

ES-MS (m/z): $[M+H^+]^+$=1310.8 and $[M+TEAH^+]^+$=1411.8, the ES-MS value corresponding to the mass over the charge of the ion detected.

Elemental analysis calculated (as %) for $C_{78}H_{78}N_4O_9S_2 \cdot 2H_2O$ (1347.70 g/mol): C, 69.51; H, 6.13; N, 4.16. found: C, 69.42; H, 6.05; N, 3.9.

EXAMPLE 2

Synthesis of Compound 2: $NTA(CysC(C_6H_5)_3OH)_3$

Compound 1 (0.310 g, 0.236 mmol) is dissolved in 6 ml of ethanol, and lithium hydroxide (LiOH) is added (0.95 ml, 0.95 mmol). The reaction mixture is then stirred for 1 h at ambient temperature, and then evaporated. The residue obtained is then dissolved in 6 ml of water, and hydrochloric acid (HCl) at 1 mol/l is added to pH=4-5.

The aqueous phase is then extracted with 15 ml of ethyl acetate.

The resulting product (0.242 g, yield=83%) is then used without further purification.

$^1H$ NMR (DMSO-$d_6$, 400 MHz, 298 K): 2.37-2.46 (m, 6H, $CH_2SC$); 3.32 (s, 6H, $CH_2CO$); 4.17-4.21 (m, 3H, CH) 7.20-7.37 (m, 45H, $C(C_6H_5)_3$); 8.46 (d, J=7.4 Hz, 3H, NH).

$^{13}C$ NMR (DMSO-$d_6$, 100 MHz, 298 K): δ=34.03 ($CH_2S$); 52.34 (CH); 60.68 ($CH_2CO$); 130.00-127.67 (($C_6H_5)_3$); 145.16 ($C(C_6H_5)_3$); 172.02 and 171.61 (2*CO)

ES-MS (m/z): $[M+Na^+]^+$=1249.2

EXAMPLE 3

Synthesis of Compound 3: $NTA(CysOH)_3$

Trifluoroacetic acid (1.77 ml, 23.8 mmol) and triethylsilane (0.456 ml, 2.85 mmol) are successively added to compound 2 (0.584 g, 0.476 mmol) in 21 ml of dichloromethane ($CH_2Cl_2$), under argon.

After stirring for 30 minutes at ambient temperature, the mixture is evaporated.

The resulting product (744.5 mg) is then purified by HPLC: $t_R$=13.75 minutes (linear gradient 95/5 to 0/100, A/B in 15 minutes).

The compound 3 obtained is a white powder (0.209 g, yield=88%).

$^1H$ NMR ($D_2O$, 400 MHz, 298 K): δ=3.07 and 3.01 (ABX, $J_{AX}$=4.3 Hz, $J_{BX}$=6.8 Hz, $J_{AB}$=14.5 Hz, 6H, $CH_2SH$); 3.81-3.90 (m, 6H, $CH_2CO$); 4.72 (t, J=5.9 Hz, 3H, CH).

$^{13}C$ NMR ($D_2O$, 100 MHz, 298 K): δ=27.86 ($CH_2SH$); 57.38 (CH); 60.07 ($CH_2CO$); 173.46 (COOH); 175.77 (NH CO).

ES-MS (m/z): $[M-H^+]^-$=499.0.

EXAMPLE 4

Synthesis of Compound 4: NTA(CysOC$_2$H$_5$)$_3$

Trifluoroacetic acid (1.81 ml, 24.4 mmol) and triethylsilane (0.47 ml, 2.9 mmol) are successively added to compound 1 (0.640 g, 0.49 mmol) in 15 ml of dichloromethane (CH$_2$Cl$_2$), under argon.

After stirring for 30 minutes at ambient temperature, the mixture is evaporated.

The resulting product (0.627 g) is then purified by HPLC: $t_R$=12.7 minutes (linear gradient 50/50 to 0/100, A/B in 15 minutes).

The compound 4 obtained is an oily white solid (0.110 g, yield=49%).

$^1$H NMR (CD$_3$CN, 500 MHz, 298 K): δ=1.25 (t, J=7.1 Hz, 9H, CH$_3$); 1.97 (t, J=8.8 Hz, 3H, SH); 2.95 and 3.00 (ABXY, $J_{AX}$=4.6 Hz, $J_{BX}$=6.1 Hz, $J_{BY}$=9.0, $J_{AY}$=9.3 Hz, $J_{AB}$=14.0 Hz, 6H, CH$_2$SH); 3.48 and 3.52 (AB, $J_{AB}$=16.3 Hz, 6H, CH$_2$CO); 4.18 and 4.22 (ABX$_3$; $J_{AX}$=7.1 Hz, $J_{BX}$=7.1 Hz, $J_{AB}$=10.8 Hz, 6H, CH$_2$—CH$_3$); 4.70 (ddd, J=4.7, 6.2 and 8.0 Hz, 3H, CH); 7.71 (d, J=8.0 Hz, 3H, NH).

$^{13}$C NMR (CD$_3$CN, 100 MHz, 298 K): δ=14.97 (CH$_3$); 27.40 (CH$_2$SH); 55.81 (CH); 59.75 (CH$_2$CO); 63.02 (CH$_2$CH$_3$); 171.61 and 172.02 (2*CO).

ES-MS (m/z): [M+H$^+$]$^+$=585.0 and [M+Na$^+$]$^+$=607.3.

EXAMPLE 5

Synthesis of Compound 5: NTA(CysC(C$_6$H$_5$)$_3$NH$_2$)$_3$

Nitriloacetic acid (0.068 g, 0.357 mmol) is added to a solution of CysC(C$_6$H$_5$)$_3$(NH$_2$) (0.401 g, 1.10 mmol) in 10 ml of dimethylformamide (DMF). The mixture is then cooled to a temperature of 0° C., and N-ethyl-N'-(3-dimethylaminopropyl)carbodiimide (0.212 g, 1.10 mmol) and 1-hydroxybenzotriazole hydrate (0.150 g, 1.11 mmol) are successively added. The reaction mixture is then mixed at ambient temperature for 24 h under argon.

After evaporation of the solvent, the residue is then washed with 25 ml of water, and then filtered. The solid is then dissolved in 100 ml of dichloromethane (CH$_2$Cl$_2$). The organic phase is then washed with 3×50 ml of water and 1×50 ml of a saturated solution of sodium chloride (NaCl).

The organic phase is then dried with sodium sulfate (Na$_2$SO$_4$), and then concentrated under reduced pressure (20 mbar) so as to give NTA(CysC(C$_6$H$_5$)$_3$(NH$_2$)$_3$) (0.404 g, yield=92%) in the form of a white powder.

$^1$H NMR (CD$_3$CN, 400 MHz, 298 K): δ=2.37-2.44 (m, 6H, CH$_2$S); 3.14 and 3.19 (AB, $J_{AB}$=16.4, 6H, CH$_2$CO); 4.00-4.06 (m, 3H, CH); 5.70 (s, 3H, NH$_2$); 6.24 (s, 3H, NH$_2$); 7.16-7.32 (m, 45H, SC(C$_6$H$_5$)$_3$); 7.85 (d, J=7.2 Hz, 3H, NH).

$^{13}$C NMR (CD$_3$CN, 100 MHz, 298 K): δ=38.89 (CH$_2$S); 57.78 (CH); 63.18 (CH$_2$CO), 132.37-134.89 ((C$_6$H$_5$)$_3$); 150.03 (C(C$_6$H$_5$)$_3$); 176.15 and 178.074 (2*CO).

ES-MS (m/z): [M+Na$^+$]$^+$=1246.2 and [M+K$^+$]$^+$=1262.2.

Elemental analysis calculated (as %) for C$_{72}$H$_{69}$N$_7$O$_6$S$_3$·H$_2$O (1242.57 g/mol): C, 69.60; H, 5.76; N, 7.89; O, 9.01; S, 7.74. found: C, 69.60; H, 5.72; N, 7.95; O, 8.65; S, 7.83.

EXAMPLE 6

Synthesis of Compound 6: NTA(CysNH$_2$)$_3$

Trifluoroacetic acid (1.4 ml, 17.84 mmol) and triethylsilane (0.54 ml, 2.14 mmol) are successively added to compound 5 (0.437 g, 0.357 mmol) in 15 ml of dichloromethane (CH$_2$Cl$_2$), under argon.

After stirring for 30 minutes at ambient temperature, the mixture is evaporated.

The resulting product (0.6 g) is then purified by HPLC: $t_R$=18.9 minutes (linear gradient 95/5 to 65/35, A/B in 25 minutes).

The compound 6 obtained is a white solid (0.065 g, yield=37%).

$^1$H NMR (D$_2$O, 500 MHz, 298 K): δ=2.87 (ABX, $J_{AX}$=4.9 Hz, $J_{BX}$=7.5 Hz, $J_{AB}$=14.2, 6H, CH$_2$SH); 3.55 (s, 6H, CH$_2$CO); 4.45 (dd, J=7.5, 3H, CH).

$^{13}$C NMR (D$_2$O, 100 MHz, 298 K): δ=28.18 (CH$_2$SH); 57.93 (CH); 60.85 (CH$_2$CO); 175.98 and 177.04 (2*CO).

ES-MS (m/z): [M+H$^+$]$^+$=498.1.

EXAMPLE 7

Synthesis of Compound 7: Ethyl 2-(2-bromoacetamido)-3-(triethylthio)propanoate

Compound 7 is synthesized according to the procedure described in the literature (*Synthesis*, 2003 (11), 1699-1704).

At a temperature of 0° C., a solution of bromoacetyl bromide (0.235 ml, 2.69 mmol) in 1 ml of dichloromethane (CH$_2$Cl$_2$) is added to a mixture of HCysC(C$_6$H$_5$)$_3$OC$_2$H$_5$ (0.996 g, 2.54 mmol) in 10 ml of dichloromethane (CH$_2$Cl$_2$) and 10 ml of a 10% aqueous solution of potassium bicarbonate (KHCO$_3$).

The reaction mixture is then stirred for 1 h at a temperature of 0° C.

After separation by settling out, the aqueous phase is extracted with 3×16 ml of dichloromethane (CH$_2$Cl$_2$).

The organic phase is dried with sodium sulfate (Na$_2$SO$_4$), and then concentrated under vacuum.

Compound 7 (1.29 g, yield=99%), which is yellow in color, is then used without further purification.

$^1$H NMR (CD$_3$CN, 400 MHz, 298 K): δ=1.29 (t, J=3.6 Hz, 3H, CH$_3$); 2.62 and 2.74 (ABX, $J_{AX}$=4.8 Hz, $J_{BX}$=6.0 Hz, $J_{AB}$=12.4 Hz, 2H, CH$_2$SC(C$_6$H$_5$)$_3$); 3.86 (s, 2H, BrCH$_2$CO); 4.23 (q, J=7.0 Hz, 2H, CH$_2$CH$_3$); 4.56 (td, J=2.4 and 7.2 Hz, 1H, CH); 6.95 (d, J=8.0 Hz, 1H, NH); 7.24-7.35 (m, 10H, SC(C$_6$H$_5$)$_3$); 7.43 (d, J=7.6 Hz, 5H, SC(C$_6$H$_5$)$_3$).

EXAMPLE 8

Synthesis of Compound 8: NOTA(CysC(C$_6$H$_5$)$_3$OC$_2$H$_5$)$_3$ 1,4,7-Triazacyclononane trihydrochloride (0.423 g, 1.77 mmol) and potassium carbonate (K$_2$CO$_3$) (1.56 g, 11.31 mmol) are successively added to a solution of compound 7 (2.90 g, 5.66 mmol) in 60 ml of anhydrous acetonitrile (CH$_3$CN).

The reaction mixture is then stirred for 16 h at ambient temperature, under argon.

After evaporation of the solvent, the residue is dissolved in a mixture of 180 ml of ethyl acetate (CH$_3$COOC$_2$H$_5$) and 100 ml of water.

The organic phase is washed with 2×70 ml of water and 70 ml of a saturated solution of sodium chloride (NaCl), dried with sodium sulfate (Na$_2$SO$_4$), and then concentrated under reduced pressure (20 mbar).

The resulting product (2.66 g) is purified by silica gel chromatography (40 ml, eluent: CH$_2$Cl$_2$/ethanol gradient ranging from 100/0 to 96/4), so as to give a compound 8 (1.99 g, yield 77%) in the form of a white powder.

$^1$H NMR (CD$_3$CN, 400 MHz, 298 K): δ=1.21 (t, J=7.0 Hz, 19H, CH$_3$); 2.58 and 2.67 (ABX, $J_{AX}$=4.9 Hz, $J_{BX}$=5.5 Hz, $J_{AB}$=12.1 Hz, 6H, CH$_2$S); 2.82 (s, 12H, N—CH$_2$—CH$_2$—N); 3.11 (s, 6H, CH$_2$CO); 4.14 (q, J=7.0 Hz, 6H, CH$_2$—CH$_3$); 4.32-4.37 (m, 3H, CH), 7.17-7.27 (m, 30H, SC(C$_6$H$_5$)$_3$); 7.33 (d, J=7.4 Hz, 15H, SC(C$_6$H$_5$)$_3$); 7.50 (d, J=8.2 Hz, 3H, NH).

$^{13}$C NMR (CD$_3$CN, 100 MHz, 298 K): δ=14.41 (CH$_3$); 34.20 (CH$_2$SC); 51.10 (CH); 57.12 and 61.98 (N—CH$_2$—CH$_2$—N); 63.01 (CH$_2$CH$_3$); 66.93 (CH$_2$CO), 128.25-129.71 ((C$_6$H$_5$)$_3$); 144.53 (C(C$_6$H$_5$)$_3$); 171.08 and 170.57 (2*CO).

ES-MS: m/z: [M+H$^+$]$^+$=1423.42 and [M+Cl$^-$]$^-$=1457.08.

Elemental analysis calculated (%) for C$_{84}$H$_{90}$N$_6$O$_9$S$_3$.H$_2$O (1441.85 g/mol): C, 69.97; H, 6.43; N, 5.83; S, 6.67. found: C, 69.75; H, 6.36; N, 5.77; S, 7.02.

EXAMPLE 9

Synthesis of Compound 9: NOTA(CysOC$_2$H$_5$)$_3$

Trifluoroacetic acid (1.25 ml, 16.85 mmol) and triethylsilane (0.325 ml, 2.02 mmol) are successively added to compound 8 (0.480 g, 0.337 mmol) in 17 ml of dichloromethane (CH$_2$Cl$_2$), under argon.

After stirring for 30 minutes at ambient temperature, the mixture is evaporated.

The resulting product (703 mg) is then purified by HPLC ($t_R$=15.6 minutes (linear gradient 80/20 to 0/100, A/B in 15 minutes)).

The compound 9 obtained is an oily solid (0.199 g, yield=84%).

$^1$H NMR (CD$_3$CN, 400 MHz, 298 K): δ=1.26 (t, J=7.3 Hz, 9H, CH$_3$); 2.85-3.06 (m, 18H, CH$_2$SH and N—CH$_2$—CH$_2$—N); 3.68 (s, 6H, CH$_2$CO); 4.13-4.24 (m, 6H, CH$_2$—CH$_3$); 4.67 (td, J=4.4 and 7.3 Hz, 3H, CH); 7.45 (d, J=8.1 Hz, 3H, NH).

$^{13}$C NMR (CD$_3$CN, 100 MHz, 298 K): δ=14.99 (CH$_3$); 27.31 (CH$_2$SH); 50.41 and 51.33 (N—CH$_2$—CH$_2$—N); 56.29 (CH); 58.93 (CH$_2$CO); 63.13 (CH$_2$CH$_3$); 170.49 and 171.38 (2*CO).

ES-MS (m/z): [M+H]$^+$=697.6.

2/ Characterization of the Copper Cu(I) Complexes

2/1—UV-Visible Spectroscopy and Circular Dichroism

The formation of the Cu(I) complexes was monitored by UV spectroscopy. The thiolate→Cu(I) charge transfer band appears clearly around 260 nm. This band increases up to 2 equivalents for the four compounds NTA(CysOC$_2$H$_5$)$_3$, NTA(CysNH$_2$)$_3$, NTA(CysOH)$_3$ and NOTA(CysOC$_2$H$_5$)$_3$. The Cu(I) complexes obtained therefore have an overall stoichiometry of 2:1 (Cu:L) for these ligands (L) comprising three cysteines.

FIG. 1 gives an example of UV quantitative determination of NTA(CysOC$_2$H$_5$)$_3$ (compound 4) with Cu(CH$_3$CN)PF$_6$ (Cu(I)) in phosphate buffer at a pH of 7.4.

The same type of quantitative determination followed by circular dichroism shows the successive formation of two complexes between 0 and 2 equivalents of Cu(I). For NTA(CysOC$_2$H$_5$)$_3$, the first complex formed does not have a band characteristic of the Cu—Cu interaction (beyond 300 nm); this first complex is therefore a mononuclear compound. The second complex formed between 1 and 2 equivalents has a band at 340 nm and is therefore a polynuclear Cu(I) copper compound.

For NOTA(CysOC$_2$H$_5$)$_3$, only polynuclear complexes are revealed.

Procedure:

Since the —SH thiol functions of the chelating agents are capable of becoming oxidized in air, all the solutions were prepared in a glovebox under an argon atmosphere. Ligand solutions were then prepared, before each experiment, using water that had been deoxygenated and purified with a Millipore Milli-Q® system containing 20 mM of a solution of phosphate buffer (pH=7.4) and of acetonitrile (v/v: 9/1).

The final concentration of the ligand solution was determined by measuring the concentration of the free thiol functions in the ligand, according to the Ellman procedure described in P. W. Riddles, R. L. Blakeley, B. Zerner, Methods Enzymol., 1983, 91, pp. 49-60. This method uses 5,5'-dithiobis-2-nitrobenzoic acid (DNTB) as indicator, each free thiol group present in the ligand producing 1 equivalent of TNB$^{2-}$ ($\epsilon^{412\,nm}$ (TNB$^{2-}$)=14 150 M$^{-1}$.cm$^{-1}$, $\epsilon^{412\,nm}$ being the molar extinction coefficient for TNB$^{2-}$ at 412 nm). The concentrations of the ligand solution are between 30 and 100 μm.

The solutions of Cu(I) copper were prepared by dissolving an appropriate amount of Cu(CH$_3$CN)$_4$ PF$_6$ in deoxygenated acetonitrile. The final concentration is determined by adding an excess of sodium bathocuproine disulfonate (Na$_2$BCS) and by measuring the absorbance of the Cu(BCS)$_2^{3-}$ ($\lambda_{max}$=483 nm, $\epsilon$=13 300 M$^{-1}$.cm$^{-1}$).

The UV-visible spectra were recorded with a Varian Cary 50 spectrophotometer, and the titrations by circular dichroism with a Chirascan spectrometer (Applied Photophysics®). 2.5 ml of the ligand solution prepared is transferred into a UV cell with a 1 cm path length, closed with a leaktight septum stopper. Aliquots corresponding to 0.1 equivalent of Cu(I) in solution in acetonitrile are added to the UV cell via a hermetic syringe (Hamilton™), so as to avoid oxidation of the thiol functions.

2/2—Molecularity of the Complexes: Diffusion Coefficients

The formation of the complexes was also monitored by $^1$H NMR at 500 MHz.

For compound 4, NTA(CysOC$_2$H$_5$)$_3$ (denoted ligand L), it clearly appears that the following complexes are formed:

a mononuclear complex: L+Cu(I)→CuL$^{2-}$ a polynuclear complex: CuL$^{2-}$+Cu(I)→(Cu$_2$L$^-$)$_n$ The diffusion coefficients for these complexes were also measured (cf. Table II). These translational diffusion coefficients are linked to the molecular mass of the compounds and make it possible to evaluate the molecularity of the complexes (P. Rousselot-Pailley, O. Sénèque, C. Lebrun, S. Crouzy, D. Boturyn, P. Dumy, M. Ferrand, P. Delangle, Inorg. Chem., 2006, 45, pp. 5510-5520). They indicate that the complexes formed with compound 4, NTA(CysOC$_2$H$_5$)$_3$, are indeed CuL and then Cu$_6$L$_3$, whereas the polymolecular species Cu$_8$L$_4$ is observed for compound 9, NOTA(CysOC$_2$H$_5$)$_3$.

TABLE II

Diffusion coefficients D for the Cu(I)-compound 4 NTA(CysOC$_2$H$_5$)$_3$ and Cu(I)-compound 9 NOTA(CysOC$_2$H$_5$)$_3$ complexes

| D (m$^2$s$^{-1}$) × 10$^{10}$ | L | CuL | (Cu$_2$L$^-$)$_n$ |
|---|---|---|---|
| Compound 4 NTA(CysOC$_2$H$_5$)$_3$ | 3.2 | 3.0 | 2.0 → n = 3 |
| Compound 9 NOTA(CysOC$_2$H$_5$)$_3$ | 3.0 | — | 1.8 → n = 4 |

Procedure:

The NMR spectra were recorded on a Bruker Avance 500 MHz spectrometer, equipped with a 3-axis-gradient 5 mm indirect proton probe. The diffusion coefficient measurements were carried out using a bipolar sequence (bipolar stimulated spin echo sequence) (A. Jershow, N. Müller, J. Magn. Reson., 1997, 125, pp. 372-375).

The diffusion coefficients were obtained using the equation:

$$I(\delta,\Delta,g)=I_0\exp[-\gamma^2 g^2\delta^2(\Delta-\delta/3)D]$$

in which:
I($\delta$, $\Delta$, g) is the intensity obtained in the presence of the gradient pulses of force g,
$I_0$ is the intensity obtained in the absence of the pulsation pulses,
$\delta$ is the length of the gradient pulse,
$\Delta$ is the diffusion time, and
$\gamma$ is the gyromagnetic ratio (for protons, $\gamma=26.7520\times10^7$ rad.$T^{-1}$.$s^{-1}$).

These competition experiments made it possible to quantify the affinity of these new chelating agents for Cu(I): the apparent complexation constants for Cu(I) at pH=7.4 in a 20 mM phosphate buffer, as defined below, are given in Table III.

$$K_{app} = \frac{[Cu]_{complexed}}{[Cu]_{free}[L]_{free}}$$

TABLE III

Results of the competition experiments for the various ligands, in a 20 mM phosphate buffer solution, pH 7.4, at a temperature of 298 K

| | Compound 3 NTA(CysOH)$_3$ | Compound 4 NTA(CysOC$_2$H$_5$)$_3$ | Compound 6 NTA(CysNH$_2$)$_3$ | Compound 9 NOTA(CysOC$_2$H$_5$)$_3$ |
|---|---|---|---|---|
| BCS equivalents* | 3.5 | 57 | 50 | 12 |
| logK$_{app}$ | 16 | 19 | 19 | 17.5 |

*Number of equivalents of BCS relative to Cu, necessary to displace 50% of the copper complexed by a ligand starting from the concentrations [Cu]$_0$ = 0.9 [L]$_o$, in a 20 mM phosphate buffer, pH 7.4, at a temperature of 298 K.

The values $\Delta$ and $\delta$ used for the diffusion coefficient measurements were respectively 100 ms and 2 ms.

In the experiments, g was incremented from 2.95 to 41.2 G.cm$^{-1}$.

The ligand samples were prepared in a 20 mM phosphate buffer solution of pH=7.4, prepared in a solution of D$_2$O and of CD$_3$CN (v/v: 9/1), at a concentration of ~1 mM. The aliquots of a solution of Cu(CH$_3$CN)$_4$PF$_6$ in CD$_3$CN were then added to the ligand sample.

2/3—Affinity Constants

The affinity of the synthesized chelating agents for Cu(I) is an important piece of data since it makes it possible to quantify the capacity of the chelating agents for complexing this ion.

The affinity constants were measured by means of a known competitor having a strong affinity for Cu(I), bathocuproine disulfonate (BCS), which forms Cu(I) complexes of known stability according to the reaction below:

Cu(I) + 2BCS = Cu(BCS)$_2$ $$K = \frac{[Cu(BCS)_2]}{[Cu][BCS]^2} = 10^{19.8}$$

(P. Rousselot-Pailley, O. Sénèque, C. Lebrun, S. Crouzy, D. Boturyn, P. Dumy, M. Ferrand, P. Delangle, Inorg. Chem., 2006, 45, pp. 5510-5520; Z. Xiao, F. Loughlin, G. N. George, G. J. Howlett, A. G. Wedd, J. Am. Chem. Soc., 2004, 126, pp. 3081-3090).

The amount of added bathocuproine disulfonate (BCS) necessary to displace 50% of the Cu(I) complexed by these ligands is a first indication of the affinity for Cu(I). The higher this percentage, the higher the affinity of the sulfur-containing ligand for Cu(I). These data immediately show that the three ligands studied can be classified according to their increasing affinity for Cu(I):

Compound 3 NTA(CysOH)$_3$<Compound 9 NOTA (CysOC$_2$H$_5$)$_3$<Compound 4 NTA(CysOC$_2$H$_5$)$_3$~Compound 6 NTA(CysNH$_2$)$_3$ It is clearly apparent that:
compound 4, NTA(CysC$_2$H$_5$)$_3$, and compound 6, NTA (CysNH$_2$)$_3$, have an extremely high affinity for Cu(I) (K$_{app}$=10$^{19}$)
the affinity is weaker for the compound comprising acid functions, compound 3, NTA(CysOH)$_3$, compared with the similar neutral ligand represented by compound 4, NTA(CysOC$_2$H$_5$)$_3$.

Procedure:

The complexes of Cu(I) copper with the ligands are quantitatively determined with bathocuproine disulfonate (BCS) with the aim of measuring their affinity constants. The complex is prepared by adding a solution of acetonitrile (CH$_3$CN) containing 0.5, 0.9 or 1.8 equivalents of Cu(I) copper to the ligand solution, in a solution of phosphate buffer at 20 mM, pH=7.4/acetonitrile (v/v: 9/1). The formation of the complex is then carried out by stirring the mixture for 10 minutes under argon.

Aliquots of a solution of bathocuproine disulfonate (BCS) in the same buffer solution are then added to the ligand-copper complex.

The UV-visible spectra are then recorded, and the absorbance stability is verified before the addition of the other aliquots.

3/ Characterization of the Complexes of Other Metal Ions

In general, the formation of a complex from a metal M and n ligands L is written:

M+nL$\rightleftharpoons$[M(L)$_n$]

Associated with this reaction is an apparent complexation constant log K$_{app}$, where:

$$K_{app}=[ML]/[M][L]_{tot}$$

in which:
[ML] is the concentration of complex,
[M] is the concentration of metal, and
[L]$_{tot}$ is the concentration of free ligand (whatever its protonated form).

This constant is expressed approximately by revealing the concentrations instead of the activities of the ions present at equilibrium, without ever revealing the solids or the solvent.

The apparent complexation constants for some of the known chelating agents are given in Table IV below:

TABLE IV

| Log $K_{app}$ at T = 298 K (at pH = 7.4) | EDTA | Trien | Pen | BAL |
|---|---|---|---|---|
| Ca(II) | 7.8 | — | — | — |
| Cu(I) | — | — | 8.3 | — |
| Cu(II) | 16.0 | 16.0 | — | — |
| Zn(II) | 13.7 | 7.9 | 5.8 | 9.0 |
| Cd(II) | 13.7 | 6.6 | 7.6 | — |
| Hg(II) | 18.7 | 20.6 | 14.9 | 21.2 |
| Pb(II) | 15.2 | 6.3 | 9.2 | — |
| Cu/Zn selectivity | 2.3 | 8.1 | 2.5 | — |
| Hg/Zn selectivity | 5 | 12.7 | 9.1 | 12.2 |

The selectivity between two metals M/M' corresponds to the selectivity of the ligand for the metal M relative to that of the metal M', this selectivity being equal to:

$$\log(K_{app}(M)/K_{app}(M'))=\log K_{app}(M)-\log K_{app}(M')$$

The chelating agents presented may also be advantageous for the complexation of certain toxic ions such as Hg(II), Cd(II) and Pb(II). A thorough study was carried out in the case of compound 4, NTA(CysOC$_2$H$_5$)$_3$, which is found to be the most powerful Cu(I)-chelating agent. Some data available for compound 9, NOTA(CysOC$_2$H$_5$)$_3$, are also given below.

3/1—Study Carried Out on Compound 4, NTA(CysOC$_2$H$_5$)$_3$

UV quantitative determinations aimed at following the appearance of the S$^-$→M charge transfer band made it possible to show that the stoichiometries of the complexes were 1:1 (M:L) for Cd(II), Zn(II), Pb(II) and Hg(II). Only the Hg(II) complex subsequently changed to another complex probably involving several metal ions (Hg$_3$L$_2$).

The affinity constants with Pb(II) were determined by analysis of the quantitative determinations of the ligands with Pb(II) in a 20 mM bis-tris buffer (2-bis(2-hydroxyethyl) amino-2-(hydroxymethyl)-1,3-propanediol) at pH=7, by means of the SPECFIT program, which uses a singular-value decomposition algorithm and fits the data according to a least squares analysis, and following the procedure described in the article by P. Rousselot-Pailley, O. Sénèque, C. Lebrun, S. Crouzy, D. Boturyn, P. Dumy, M. Ferrand, P. Delangle, Inorg. Chem., 2006, 45, pp. 5510-5520, taking into account the affinity of the buffer for Pb(II).

The affinity constants with the Cd(II), Zn(II) and Ca(II) ions were subsequently determined by titrating the Pb(II) complex with a second metal ion according to the following competition reaction:

PbL+M→Pb+ML

For Hg(II), which has a very high affinity for thiolate ligands, we performed a competition with EDTA having a known affinity constant (cf. Table IV) according to the following reaction:

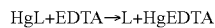

TABLE V

Apparent stability constants for the M.NTA(CysOC$_2$H$_5$)$_3^-$ complexes at pH = 7, at a temperature of 298 K

| | log $K_{app}$ (at pH = 7) | $\lambda_{max}$ (nm) | $\epsilon$ (cm$^{-1}$M$^{-1}$) |
|---|---|---|---|
| Ca(II) | <3 | — | — |
| Zn(II) | 9.1 | 220 | 15 800 |
| Cd(II) | 10.6 | 250 | 20 000 |
| Hg(II) | >22.5 | 237 | 15 000 |
| Pb(II) | 8.9 | 349 | 5 500 |

Procedure:

The procedure is the same as that followed above in paragraph 2/1—.

The metal solutions are prepared using the corresponding salt (CaCl$_2$, CdCl$_2$, PbCl$_2$ or ZnCl$_2$) in a 20 mM bis-tris buffer solution at pH=7, and titrated with a 5 mM EDTA solution in the presence of a calorimetric indicator.

For the titrations, the aliquots of the Ca(II), Cd(II) or Zn(II) solutions are added to the UV cell containing a peptide/lead complex in a 20 mM bis-tris buffer solution at pH=7, obtained using 1 equivalent of ligand and 3 equivalents of Pb(II). The experiment is carried out until the signal corresponding to the peptide/lead complex disappears, or until the peptide/lead complex signal is less than 10%. For Ca(II), no change in the spectrum of the lead complex was observed, even for 1000 equivalents of Ca(II) added relative to the ligand.

The spectra were analyzed using the SPECFIT program, as above.

The bis-tris buffer solution was chosen because it forms a stable and soluble complex with Pb(II), thus preventing the formation and precipitation of Pb(OH)$_2$ (J. C. Payne, M. A. terHorst, H. A. Godwin, J. Am. Chem. Soc, 1999, 121, pp. 6850-6855). Since the affinity of the metal ions for the bis-tris buffer solution is, moreover, known, it was included as a parameter in the adjustment (log β1=2.25 for Ca(II), 2.47 for Cd(II), 2.38 for Zn(II) and 4.32 for Pb(II) (K. H. Scheller, T. H. Abel, P. E. Polanyi, P. K. Wenk, B. E. Fischer, H. Sigel, Eur. J. Biochem., 1980, 107, pp. 455-466)).

For the titration with Ca(II), no change in the LMCT band for the Pb(II) complex was demonstrated, thus the data were simulated with less than 1% of Pb(II), which made it possible to obtain an upper limit for the apparent affinity constant log β$_{CaNTACys(OC_2H_5)_3}$<3.

A solution of mercury is prepared by dissolving HgCl$_2$ in water. An HgL complex is formed by adding aliquots of this mercury solution to a solution of ligand in a 20 mM phosphate buffer solution at pH=7.4, up to 0.9 equivalent. The change in the LMCT band for Hg(II) at 290 nm is subsequently followed by titration with a 5 mM solution of Na$_2$EDTA. No change in this band is observed up to 63 equivalents of EDTA added. These data were simulated with less than 5% of Hg(II) displaced by the EDTA, which gives an apparent affinity constant log β$_{HgNTACys(OC_2H_5)_3}$>22.5.

3/2—Study Carried Out on Compound 9 NOTA (CysOC$_2$H$_5$)$_3$

The same procedure as for compound 4 enabled us to evaluate the following affinities:

TABLE VI

Apparent stability constants for the M.NOTA (CysOC$_2$H$_5$)$_3^-$ complexes at pH = 7, at a temperature of 298 K

| | log K$_{app}$ (at pH = 7) | $\lambda_{max}$ (nm) | $\epsilon$ (cm$^{-1}$M$^{-1}$) |
|---|---|---|---|
| Ca(II) | — | — | — |
| Zn(II) | 8-10 | — | — |
| Cd(II) | 8-10 | — | — |
| Hg(II) | — | 240 | 14 000 |
| Pb(II) | 10 | 342 | 3 700 |

Advantages of the Chelating Agents of the Invention in Comparison with Other Known Chelating Agents:

Table VII gives the affinity constants measured with the chelating agents of the invention. The values measured with a model peptide (P$^C$) of the Cu(I) copper-binding loop of a metallochaperone, Atx1 (a protein involved in Cu(I) copper transport), are also given, for comparison with the proteins that chelate Cu(I) naturally in the cells.

The P$^C$ ligand binds the metal ions by virtue of two thiolate functions of two cysteines inserted in an amino acid sequence MxCxxC. The introduction of three cysteines into compound 4, NTA(CysOC$_2$H$_5$)$_3$; compound 6, NTA(CysNH$_2$)$_3$; and compound 9, NOTA(CysOC$_2$H$_5$)$_3$, made it possible to obtain stable complexes of very high selectivity with respect to the potentially competing essential ions, Ca(II) and Zn(II).

TABLE VII

Summary of affinity constants with the cysteine chelating agents

| log K$_{app}$ | p$^c$ | Compound 4 NTA(CysOC$_2$H$_5$)$_3$ | Compound 9 NOTA(CysOC$_2$H$_5$)$_3$ |
|---|---|---|---|
| Ca(II) | — | <3 | — |
| Cu(I) | 16.5 | 19 | 17.5 |
| Cu(II) | — | — | — |
| Zn(II) | 6.8 | 9.1 | 8-10 |
| Cd(II) | 9.2 | 10.6 | 8-10 |
| Hg(II) | >18.6 | >22.5 | |
| Pb(II) | 8.0 | 8.9 | 10 |
| Cu/Zn Sel. | 9.7 | 9.9 | 7.5-9.5 |
| Cu/Ca Sel. | — | >16 | — |
| Hg/Zn Sel. | >11.8 | >13.4 | — |
| Hg/Ca Sel. | | >19.5 | |

In order to show the advantage of the chelating agents of the invention, we compared the data obtained, listed in Table VII, with those known for listed known commercial chelating agents (cf. Table IV).

For Compound 4, NTA(CysOC$_2$H$_5$)$_3$:

The affinity of compound 4, NTA(CysOC$_2$H$_5$)$_3$, for Cu(I) and Hg(II) ions is very high. This ligand complexes copper better than EDTA and Trien, and is a very effective Hg(II)-complexing agent, with a higher affinity than the other chelating agents tabulated.

An important point for the use of chelating agents in vivo is their selectivity with respect to essential ions such as Ca(II) and Zn(II). There again, the selectivities measured for compound 4, NTA(CysOC$_2$H$_5$)$_3$, are much greater than those of the known chelating agents.

For Compound 9, NOTA(CysOC$_2$H$_5$)$_3$:

Fewer data were measured with this ligand. Nevertheless, a strong affinity between compound 9, NOTA(CysOC$_2$H$_5$)$_3$, and Cu(I) and also an advantageous selectivity for copper compared with zinc may be noted. Its properties are therefore very advantageous in comparison with EDTA and Trien.

The compounds of the invention have affinities and selectivities which make them very promising for the selective complexation of Cu(I), having an oxidation state which is favored in the intracellular medium, and which can be targeted for diseases such as Wilson's or Alzheimer's disease. These compounds may also be candidates for the selective complexation of mercury in cases of poisoning with this metal.

The invention claimed is:

1. Compounds of formula (I) below:

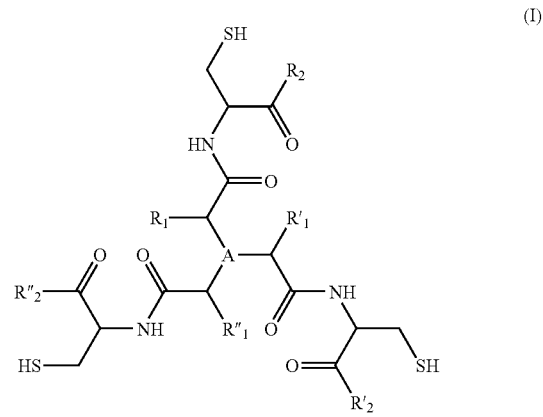

(I)

in which the group A represents:
either a nitrogen atom,
or a ring corresponding to the formula below, and in which the substitution takes place on the nitrogen atoms:

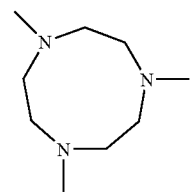

and in which:
the R$_1$, R'$_1$, and R"$_1$ radicals, which may be identical or different, represent a hydrogen atom or an optionally substituted alkyl radical containing 1 to 12 carbon atoms,
the R$_2$, R'$_2$ and R"$_2$ radicals, which may be identical or different, are chosen from —OH, —OR, —NHR and —NRR' groups in which R and R', which may be identical or different, represent a hydrogen atom or an optionally substituted alkyl radical containing 1 to 12 carbon atoms, the R$_2$, R'$_2$ and R"$_2$ radicals preferably being —NH$_2$, —OH or —OR groups in which R represents a hydrogen atom or an optionally substituted alkyl radical containing 1 to 12 carbon atoms.

2. Compounds of formula (I) according to claim 1, in which the R$_1$, R'$_1$ and R"$_1$, radicals are hydrogen atoms.

3. Compounds of formula (I) according to claim 1, in which the R$_2$, R'$_2$ and R"$_2$ radicals are —NH$_2$, —OH or —OR groups in which R represents a hydrogen atom or an optionally substituted alkyl radical containing 1 to 12 carbon atoms.

4. Compounds of formula (I) according to claim 3, in which the R$_2$, R'$_2$ and R"$_2$ radicals are —OR groups in which R is an ethyl radical.

5. Compounds of formula (I) according to claim 1, corresponding to the specific formula ($I_a$) below:

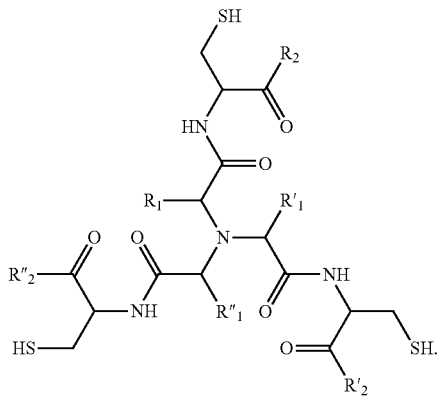

6. Compounds of formula (I) according to claim 1, corresponding to the specific formula ($I_b$) below:

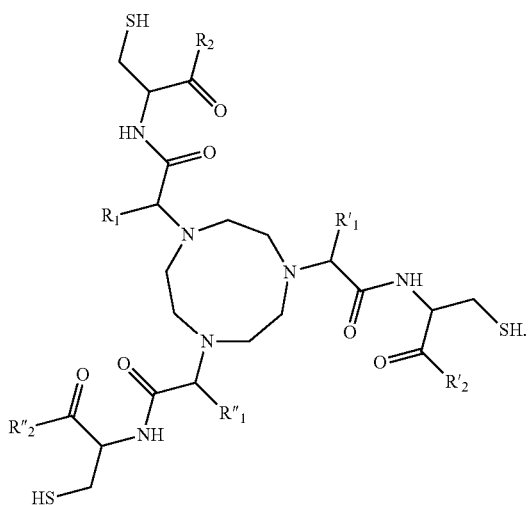

7. Method for preparing the compounds of formula ($I_a$) as defined in claim 5, characterized in that it comprises the following stages:
(i) reacting one equivalent of nitrilotriacetic acid with three equivalents of a cysteine derivative of formula:

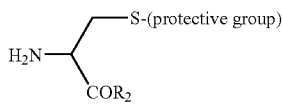

in the presence of a polar solvent, such as dimethylformamide, dichloromethane, chloroform, methanol or ethanol, preferably at a temperature of between −10° C. and 30° C., for a period of between 12 and 48 hours,
(ii) optionally, hydrolyzing the —$COR_2$ function of the product obtained during stage (i) to give an acid function by addition of a strong base,
(iii) deprotecting the —S-(protective group) function to give a thiol —SH function.

8. Method for preparing the compounds of formula ($I_b$) as defined in claim 6, characterized in that it comprises the following stages:
(i) reacting one equivalent of a molecule $R_b CHR_1 C(O) R_a$, wherein:
Ra is selected from halogen atoms, hydroxyl —OH groups and —OCORa' groups in which Ra' represents an optionally substituted alkyl group having 1 to 12 carbon atoms, Ra' preferably being a methyl or ethyl group,
$R_b$ is selected from halogen atoms, tosylate groups, and mesylate groups,
with one equivalent of a cysteine derivative of formula:

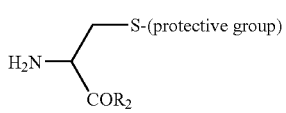

in the presence of a weak base, and in a solvent medium, said solvent being chosen from polar solvents and water, at a temperature of between −10° C. and 10° C., for a period of between 30 minutes and 2 hours,
(ii) reacting one equivalent of 1,4,7-triazacyclononane with three equivalents of a bromoacetamide derivative, obtained during stage (i), of formula:

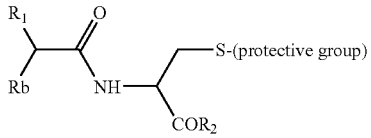

in the presence of a weak base, and in a solvent medium, said solvent being chosen from dichloromethane, chloroform, ethyl acetate, acetonitrile and dimethylformamide,
(iii) deprotecting the —S-(protective group) function to give a thiol —SH function.

9. Compounds that can be used as agents that are precursors of the compounds of formula (I) as defined in claim 1, corresponding to formula (II) below:

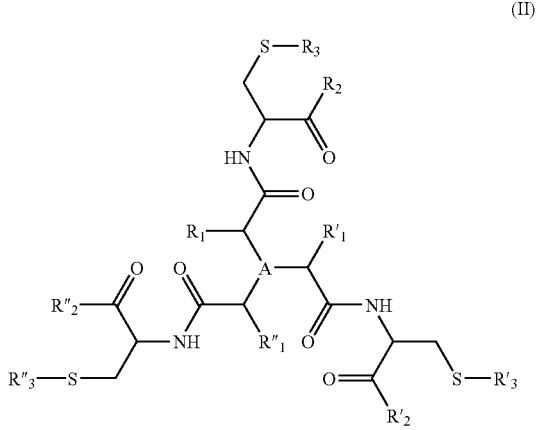

in which the group A represents:
either a nitrogen atom, or a ring corresponding to the formula below, and in which the substitution takes place on the nitrogen atoms:

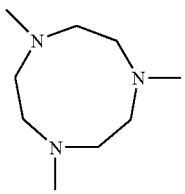

and in which:
- the $R_1$, $R'_1$, and $R''_1$, radicals, which may be identical or different, represent a hydrogen atom or an optionally substituted alkyl radical containing 1 to 12 carbon atoms,
- the $R_2$, $R'_2$ and $R''_2$ radicals, which may be identical or different, are chosen from —OH, —OR, —NHR and —NRR' groups in which R and R', which may be identical or different, represent a hydrogen atom or an optionally substituted alkyl radical containing 1 to 12 carbon atoms,
- the $R_3$, $R'_3$ and $R''_3$ radicals, which may be identical or different, represent a group —S—W or —S-E-L, wherein:
  - S is a sulfur atom,
  - W is an optionally substituted alkyl radical containing 1 to 12 carbon atoms,
  - E is a spacer arm that can be selected from optionally substituted alkyl groups containing 1 to 12 carbon atoms, and polyols,
  - L is a biological ligand.

10. Compounds of formula (II) according to claim 9, in which the $R_1$, $R'_1$, and $R''_1$, radicals are hydrogen atoms.

11. Compounds of formula (II) according to claim 9, in which the $R_2$, $R'_2$ and $R''_2$ radicals are —$NH_2$, —OH or —OR groups in which R represents a hydrogen atom or an optionally substituted alkyl radical containing 1 to 12 carbon atoms.

12. Compounds of formula (II) according to claim 11, in which the $R_2$, $R'_2$ and $R''_2$ radicals are —OR groups in which R is an ethyl radical.

13. Compounds of formula (III) below:

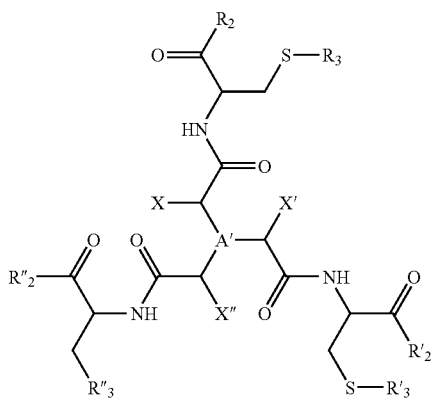

(III)

in which the group A' represents:
- either a nitrogen atom,
- or a ring corresponding to the formula below,
and in which the substitution takes place on the nitrogen atoms:

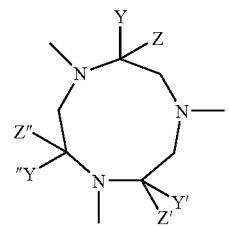

and in which:
- the $R_2$, $R'_2$ and $R''_2$ radicals, which may be identical or different, are chosen from —OH, —OR, —NHR and —NRR' groups in which R and R', which may be identical or different, represent a hydrogen atom or an optionally substituted alkyl radical containing 1 to 12 carbon atoms,
- the $R_3$, $R'_3$ and $R''_3$ radicals, which may be identical or different, represent a group —S—W or —S-E-L, wherein:
  - S is a sulfur atom,
  - W is an optionally substituted alkyl radical containing 1 to 12 carbon atoms,
  - E is a spacer arm that can be selected from optionally substituted alkyl groups containing 1 to 12 carbon atoms, and polyols,
  - L is a biological ligand,
  - the groups X, X', X", Y, Y', Y", Z, Z' and Z", which may be identical or different, represent a hydrogen atom or a label, provided that at least one of said groups X, X', X", Y, Y', Y", Z, Z' or Z" is a label.

14. Compounds of formula (III) according to claim 13, in which the $R_2$, $R'_2$ and $R''_2$ radicals are —$NH_2$, —OH or —OR groups in which R represents a hydrogen atom or an optionally substituted alkyl radical containing 1 to 12 carbon atoms.

15. Compounds of formula (III) according to claim 14, in which the $R_2$, $R'_2$ and $R''_2$ radicals are —OR groups in which R is an ethyl radical.

16. A pharmaceutical composition, characterized in that it comprises, as active ingredient, at least one compound of formula (I) as defined according claim 1, and at least one pharmaceutically acceptable carrier.

17. A pharmaceutical composition, characterized in that it comprises, as active ingredient, at least one compound of formula (II) as defined according claim 9, and at least one pharmaceutically acceptable carrier.

18. A pharmaceutical composition, characterized in that it comprises, as active ingredient, at least one compound of formula (III) as defined according claim 13, and at least one pharmaceutically acceptable carrier.

* * * * *